US010219922B2

(12) United States Patent
Robison

(10) Patent No.: US 10,219,922 B2
(45) Date of Patent: Mar. 5, 2019

(54) DEVICES AND METHODS FOR APPROXIMATING THE CROSS-SECTIONAL PROFILE OF VASCULATURE HAVING BRANCHES

(75) Inventor: Aaron Robison, Phoenix, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 0 days.

(21) Appl. No.: 13/572,328

(22) Filed: Aug. 10, 2012

(65) Prior Publication Data
US 2013/0211505 A1 Aug. 15, 2013

Related U.S. Application Data

(60) Provisional application No. 61/523,225, filed on Aug. 12, 2011.

(51) Int. Cl.
A61F 2/82 (2013.01)
A61F 2/852 (2013.01)
(Continued)

(52) U.S. Cl.
CPC ............ A61F 2/852 (2013.01); A61F 2/07 (2013.01); A61F 2/848 (2013.01); A61F 2/856 (2013.01); A61F 2/89 (2013.01); A61F 2002/061 (2013.01); A61F 2002/067 (2013.01); A61F 2002/075 (2013.01); A61F 2230/0034 (2013.01); A61F 2250/0063 (2013.01)

(58) Field of Classification Search
CPC ....................................................... A61F 2/82
USPC ................................................ 623/1.15, 1.35
See application file for complete search history.

(56) References Cited

U.S. PATENT DOCUMENTS 5,316,023 A 5/1994 Palmaz et al.
6,524,336 B1 2/2003 Papazolgou et al.
(Continued)

FOREIGN PATENT DOCUMENTS

EP 1047356 11/2000
WO 97/25001 7/1997
(Continued)

OTHER PUBLICATIONS

International Search Report and Written Opinion for PCT/US2012/050443 dated Nov. 21, 2012, corresponding to U.S. Appl. No. 13/572,328.
(Continued)

Primary Examiner — Matthew Schall

(57) ABSTRACT

This disclosure is related to devices and related methods for isolating a treatment region in a human body from fluid pressure. In various embodiments, an implantable device for isolating a treatment region in a human body from fluid pressure comprises a first elongated segment, and a second elongated segment, and one or more branch segments in fluid communication with one of the first elongated segment and the second elongated segment. The elongated segments have a combined cross section that is substantially conformable to an intraluminal cross section of a body lumen into which they are implanted. A method of installing an implantable medical device into the body of a patient comprises deploying a first elongated segment, deploying a second elongated segment, and deploying one or more branch segments in a target region of a vasculature.

23 Claims, 15 Drawing Sheets

(51) Int. Cl.
- *A61F 2/07* (2013.01)
- *A61F 2/848* (2013.01)
- *A61F 2/856* (2013.01)
- A61F 2/06 (2013.01)
- A61F 2/89 (2013.01)

(56) References Cited

U.S. PATENT DOCUMENTS

| | | | |
|---|---|---|---|
| 2001/0003161 | A1 | 6/2001 | Vardi et al. |
| 2003/0130720 | A1* | 7/2003 | DePalma et al. ............ 623/1.13 |
| 2009/0287145 | A1 | 11/2009 | Cragg et al. |
| 2009/0319029 | A1 | 12/2009 | Evans et al. |
| 2011/0130820 | A1 | 6/2011 | Cragg et al. |
| 2011/0130824 | A1* | 6/2011 | Cragg ...................... A61F 2/07 623/1.15 |
| 2012/0203329 | A1 | 8/2012 | Heuser |
| 2013/0103134 | A1 | 4/2013 | Minion |

FOREIGN PATENT DOCUMENTS

| | | |
|---|---|---|
| WO | 03/082153 | 10/2003 |
| WO | 2004/096092 | 11/2004 |
| WO | 2010/113138 | 10/2010 |

OTHER PUBLICATIONS

European Search Report from Application No. 16160971.4, dated Jul. 18, 2016, 7 pages.

Castelli, P. et al. Hybrid treatment for juxtarenal aortic occlusion: Successful revascularization using iliofemoral semiclosed endarterectomy and kissing-stents technique. Journal of Vascular Surgery, 2005; vol. 42, #3; 559-563.

Damelou, A. et al. Double-barrel stenting of distal left main stenosis in a patient with acute coronary syndrome: Intravascular ultrasound and optical coherence tomography follow-up at six months. Can J Cardiol vol. 26 No. 7 Aug./Sep. 2010; 282-285.

Kolvenbach RR., et al. Urgent Endovascular Treatment of Thoracoabdominal Aneurysms Using a Sandwich Technique and Chimney Grafts—A Technical Description. Eur J Vasc Endovasc Surg (2010), 1-7.

Kobayashi, Y., et al. Modified "T" Stenting: A Technique for Kissing Stents in Bifurcational Coronary Lesion. Catheterization and Cardiovascular Diagnosis 43:323-326 (1998).

Laborde, J.C., et al., A Novel 14F Endograft for AbdominalAortic Aneurysm: First in Man. Catheterization and Cardiovascular Interventions 76:1059-1064 (2010).

Mathisen, SR., et al. Kissing Stents in the Common Femoral Artery Bifurcation for Critical Limb Ischemia: Technical Description and Report of Three Cases. Vasc, vol. 15, # 4,211-214,2007.

Ohrlander, T. et al. The Chimney Graft: A Technique for Preserving or Rescuing Aortic Branch Vessels in Stent-Graft Sealing Zones. J Endovasc Ther, 2008;15:427-432.

Rancic, Z., MD,PHD, et al. Periscope graft to extend distal landing zone in ruptured thoracoabdominal aneurysms with short distal necks. J of Vasc Surg, 2010;51:1293-6.

Saker, MB., et al. Early Failure of Aortoiliac Kissing Stents: Histopathologic Correlation. JVIR 2000; 11:333-336.

Wachter, K. Side Vessel Drives Stent Choice for Bifurcations. Cardiology News. Jul. 2006; 16.

Yilmaz, S. et al. Aortoiliac Kissing Stents: Long-term Results and Analysis of Risk Factors Affecting Patency. J Endovasc Ther, 2006;13:291-301.

* cited by examiner

DEVICES AND METHODS FOR APPROXIMATING THE CROSS-SECTIONAL PROFILE OF VASCULATURE HAVING BRANCHES

PRIORITY CLAIM

This application claims priority to U.S. Provisional Application No. 61/523,225, entitled "SYSTEMS FOR THE REDUCTION OF LEAKAGE AROUND MEDICAL DEVICES AT A TREATMENT SITE" filed on Aug. 12, 2011, which is hereby incorporated by reference in its entirety.

BACKGROUND

Field

This disclosure relates to devices and methods for isolating a treatment region from fluid pressure, and more specifically, to providing medical devices that adaptably approximate the cross-sectional profile of the vasculature in an area of the vasculature having branch vessels and/or an irregular configuration.

Discussion of the Related Art

Treatment of various portions of the vasculature may require the installation of one or more medical devices. In this regard, a medical device can be any device or structure configured to provide and/or support a therapeutic use in the vasculature. Commercially available devices generally possess specific requirements with regard to the dimensions and configuration of the region to be treated. However, the cross-sectional profile and configuration of the primary vessel being treated, the locations at which branch vessels join the primary vessel with respect to the treatment site, and the configuration and condition of branch vessels may vary considerably on a patient-by-patient basis in a manner that can significantly affect patient eligibility for treatment with available devices. For example, in an abdominal aorta with an aneurysm, the distance between the renal arteries and the aneurysm and the length of normal-diameter iliac artery available for proximal and distal attachment can significantly affect patient eligibility for available stent devices. Angulation of the attachment site between the renal arteries and the aneurysm can also present significant limitations to treatment with commercial devices. The status and size of the iliofemoral arteries and their capacity to accommodate insertion of medical devices may impose a further limitation on a patient's eligibility for treatment with a particular medical device. Variations in the anatomical limitations presented by individual patients in combination with the limitations of available devices impose a significant limitation on patient eligibility for treatment with implantable medical devices.

For example, FIGS. 1A-1D illustrate a range of possible configurations of an abdominal aorta. FIG. 1A illustrates a vasculature 101A comprising an abdominal aorta without an aneurysm as well as major branch arteries, including the renal arteries 110, the superior mesenteric artery ("SMA") 111, the celiac artery 112, the common iliac arteries 113, the external iliac arteries 114, and the internal iliac arteries 115. FIG. 1B illustrates a vasculature 101B having a "textbook" abdominal aortic aneurysm ("AAA") 102 with a length of normal aorta proximal (closer to the heart) to the site of the aneurysm and distal (further from the heart) to the renal arteries, a region referred to as the infrarenal aortic neck 103. An AAA as illustrated in FIG. 1B may be treated with any of a number of commercially available implantable medical devices that require a length of normal infrarenal aorta for proximal attachment of the device within the vasculature.

FIG. 1C illustrates a vasculature 101C having a pararenal AAA, wherein the aorta lacks a length of normal aorta between the aneurysm and the renal arteries. A patient having a pararenal AAA may be ineligible for treatment with various commercially available devices that require a length of normal infrarenal aorta for proximal attachment and implantation. Alternatively, a patient with a pararenal AAA can be treated using chimney or sandwich graft approaches. These approaches may increase a risk of leakage around the devices at the treatment site or of device migration.

FIG. 1D illustrates a vasculature 101D having an angulated infrarenal aortic neck 104. As for a pararenal AAA, an abdominal aorta with angulation of the infrarenal aortic neck presents significant challenges for treatment with implantable medical devices, as most commercially available medical devices may be unable to conform to the cross-sectional profile of the vasculature. Moreover, the flow through the lumens defined by such medical devices may be suboptimal because the cross-sectional profile created by the medical devices at the treatment site may not substantially approximate the cross-sectional profile of the vasculature.

Thus, a need exists for devices that are adaptable to a variety of anatomical configurations to expand the scope of patient eligibility for treatment and to enhance the performance of medical devices implanted into a body lumen, particularly in patients having irregular or tortuous anatomies.

SUMMARY

In general, the present disclosure provides devices and related methods for isolating a treatment region in a human body from fluid pressure. For example, in various embodiments, a branched stent device for treatment of an abdominal aortic aneurysm is provided that includes two elongated segments and at least one branch segment in fluid communication with an elongated segment. In this example, a combined cross section of the elongated segments is substantially conformable to an intraluminal cross section of the aorta proximal to the aneurysm, thus isolating the aneurysm from fluid pressure and permitting fluid flow to distal regions through the elongated segments as well as to a branch vessel connected by the branch segment.

A device in accordance with various embodiments can include, for example, such other features as the ability to position one elongated segment independently from another elongated segment, longitudinally displaced elongated segments, modular attachment of branch segments to the elongated segments, and connectors having various structures.

A related method for installing an implantable medical device comprises, in various embodiments, deploying a first elongated segment and a second elongated segment in a target region of the vasculature and deploying a branch segment in a branch vessel, wherein a combined cross section of the first and second elongated segment is substantially conformable to an intraluminal cross section of the vasculature.

A method for installing an implantable medical device in accordance with various embodiments can further involve such steps as deploying additional branch segments, repositioning an elongated segment, positioning an open stent region of an elongated segment, deploying a connector, and the like.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure.

DETAILED DESCRIPTION OF THE ILLUSTRATED EMBODIMENTS

Figure 1A:
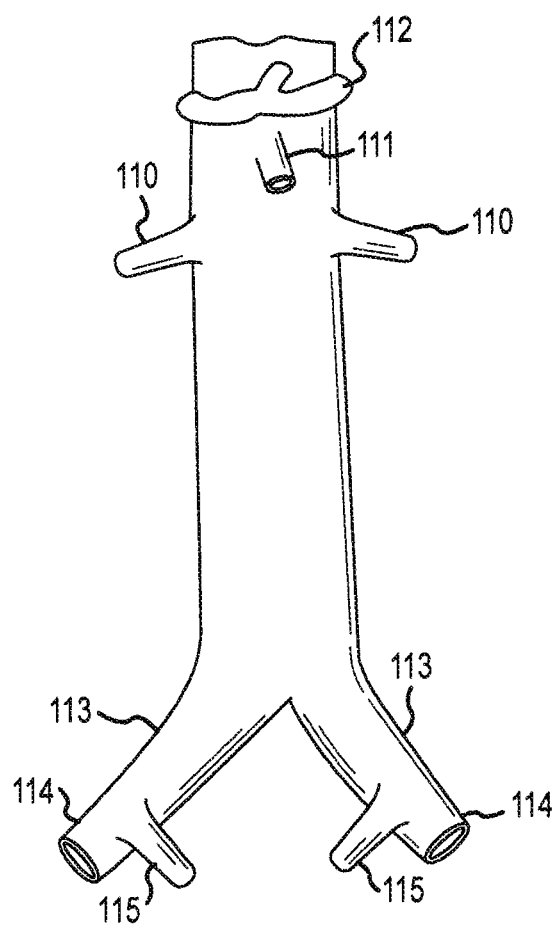
FIGS. 1A-1D illustrate profile views of vasculature comprising abdominal aortas demonstrating a range of conditions and configurations.
Figure 1B:
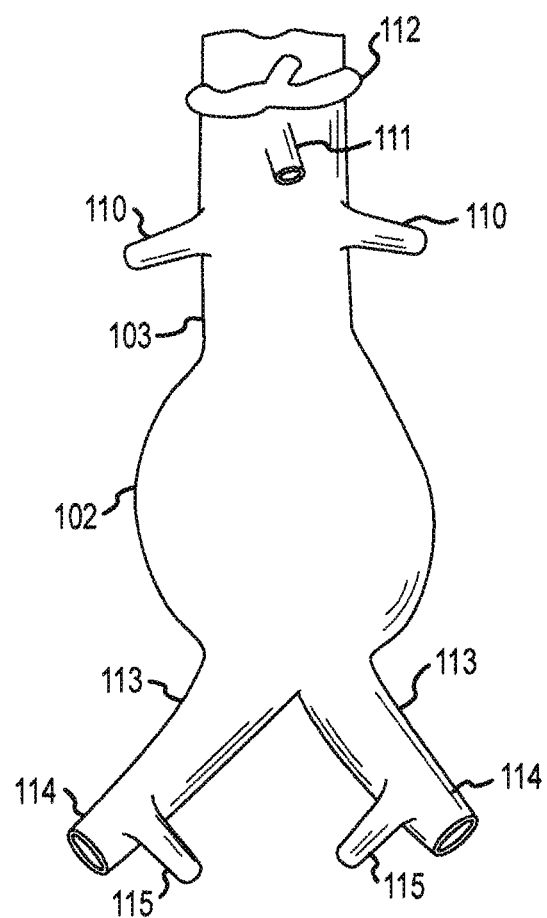
Figure 1C:
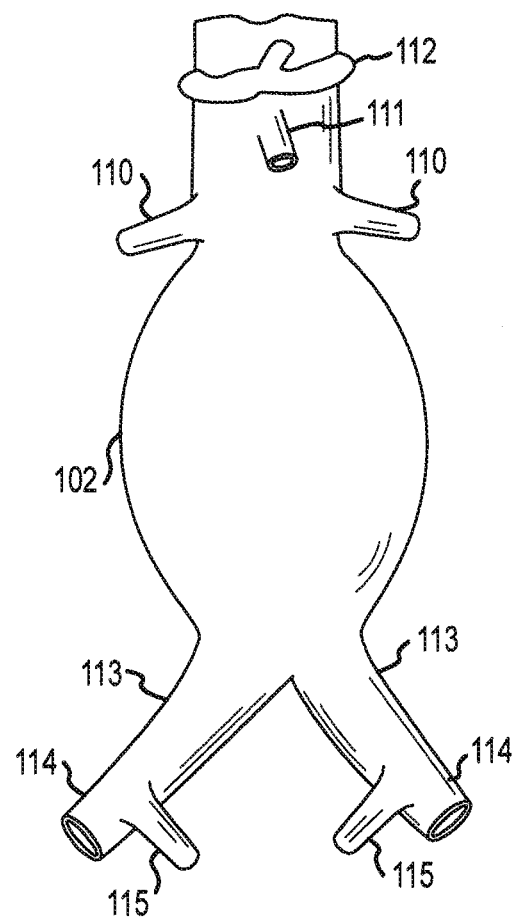
Figure 1D:
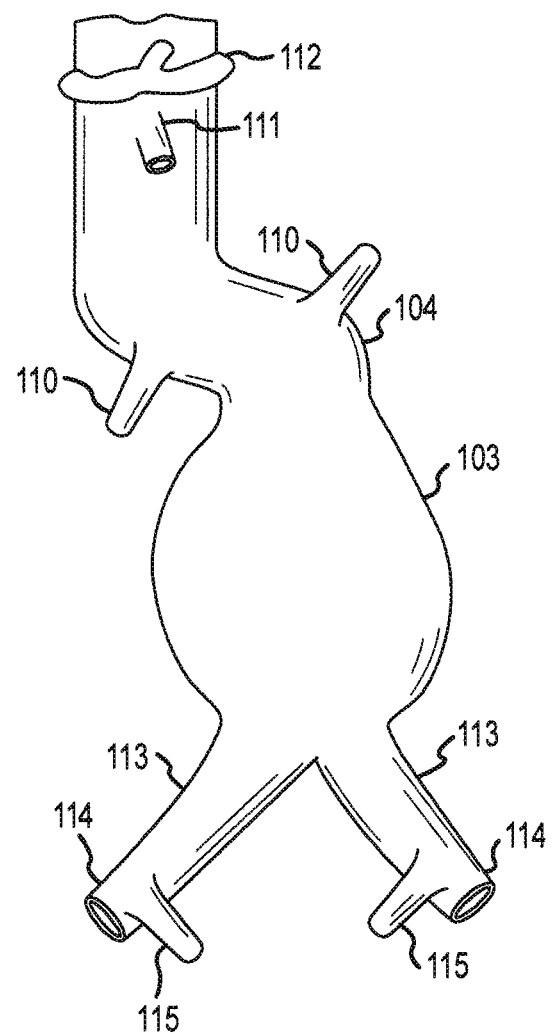

The detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments may be realized and that mechanical and other changes may be made without departing from the spirit and scope of the present disclosure. Furthermore, any reference to singular includes plural embodiments, and any reference to more than one component may include a singular embodiment. Likewise, any ordination of a device or of a component or portion of a device with designations such as "first" and "second" is for purposes of convenience and clarity and should not be construed as limiting or signifying more than an arbitrary distinction. Moreover, recitation of multiple embodiments having stated features is not intended to exclude other embodiments having additional features or other embodiments incorporating different combinations of the stated features.

As used herein, "medical devices" can include, for example stents, grafts, and stent-grafts, (whether single, multicomponent, bifurcated, branched, etc.), catheters, valves, and drug-delivering devices, to name just a few, that are implanted, acutely or chronically, in the vasculature or other body lumen or cavity at a treatment region.

As used herein, "leakage" means the unwanted or undesirable flow into or through a treatment region, where the flow is outside the lumen(s) or body(ies) defined by the medical device(s), for example into or through an area such as a "gutter" located between a portion of a device and the adjacent body tissue, between two devices, or at an intersection of a portion of one or more devices and the adjacent body tissue. As used herein, the term "endoleak" is synonymous with "leakage" and may be used interchangeably with "leakage."

As used herein, an "elliptical" shape refers to any shape that generally lacks a point where two lines, curves, or surfaces converge to form an angle. An "elliptical" shape encompasses traditional Euclidian geometric shapes such as circles and ellipses, as well as other non-angular shapes (that lack any angles), even if those shapes do not have designations common in Euclidian geometry.

As used herein, a "non-elliptical" shape refers to any shape that includes at least one point where two lines, curves, or surfaces converge to form an angle. A "non-elliptical" shape encompasses traditional Euclidian geometric shapes such as triangles, squares, and rectangles, as well as other angular shapes (that have at least one angle) such as crescents, even if those shapes do not have designations common in Euclidian geometry.

As used herein, "circumference" means the boundary line formed by an object, including, for example, an end of a stent or a stent wall at a cross section anywhere along the length of the stent. A "circumference" can include a boundary line formed by an object having any shape, including elliptical and non-elliptical shapes as defined herein, wherein the shape generally describes a line that encloses an area. A "circumference" can include a boundary line formed by an object or a cross section thereof regardless of whether the actual surface or cross section of the object described by the boundary is continuous or interrupted. For example, an open stent or an object comprising a series of separate segments that may or may not physically overlap or make contact with each other can still describe a "circumference" as used herein.

As used herein, "substantially conformable" refers to the capacity of an object to dimensionally conform to another object. The term "substantially conformable" as used herein can describe an object that is designed and given a predetermined structure and shape that fits into or against another shape, objects that have predetermined shapes that are at least in part in complementary to one another while other portions of the objects may have a shape capable of flexibly and adaptably changing to conform to another object, and objects that generally have the capacity to adapt in shape and/or conformation to other objects without any requirement for designed or predetermined complementarity to another device or object.

As used herein, "independently positionable" refers to a capacity of one component to be inserted, located, moved, and or positioned separately from another component of a device or system. The term "positionable" includes movement of any type, for example, longitudinal, lateral, rotational, and torsional movements as well as flexing, articulating, and longitudinal and radial expansion and contraction.

As used herein, "reconstrain" refers to a process that involves the reverse of deploying a medical device to an implanted state. "Reconstrain" as used herein has an equivalent meaning to such similar terms as "recapture" and "recover." "Reconstraining" a device can involve partially or fully reversing a deployment of a device by such means as replacing a sheath around the device, compacting the device onto a catheter, or otherwise putting the device back in a contracted, compressed, or restricted state. "Reconstraining" may be necessary in certain procedures or using certain devices to reposition, retract, or remove a device.

Repositioning can include, for example, longitudinal, lateral, and/or rotational movement of the device within the treatment site.

The present disclosure relates to a number of non-limiting embodiments, each of which may be used alone or in coordination with one another. A device in accordance with various embodiments can be any suitable medical device or devices installable within the vasculature or other body lumens and configured to provide for isolation of a treatment region from fluid pressure. In various embodiments, a device can comprise one or more elongated segments that substantially approximate the cross-sectional profile of the vasculature when implanted in a treatment region.

In various embodiments, the devices disclosed herein may comprise a covering material. A covering material may be any biocompatible or biodegradable material, as described in detail elsewhere herein. A covering material in accordance with various embodiments forms a generally continuous surface or surfaces of a component of the device, defining a lumen and an outer surface of the component of the device. The covering material need not be completely continuous, but may be interrupted by openings at the ends of the elongated segments or branch segments, open stent regions, and/or fenestrations such as side branch openings. The covering material may be applied to the device by any of a variety of methods, including, for example, wrapping, forming, or molding a covering material about a mandrel.

In accordance with various embodiments, a device may comprise such features as radiopaque markers or similar features that aid visualization of the device within the body during deployment and positioning.

In various embodiments, a device may comprise coatings. The coatings of the device components may be in contact with other objects including other devices or device components or interior surfaces of the vasculature, such that the combined cross-section of a first elongated segment and a second elongated segment more are substantially conformable to the intraluminal cross-sectional of the vasculature.

In various embodiments, the devices disclosed herein may comprise a support structure (e.g., a stent of any suitable configuration). The support structure may be any suitable material including, for example, stainless steel, nitinol, and the like. The support structure may comprise a plurality of stent rings. The stent rings may be operatively coupled to one another with a wire. A wire used to couple stent rings may attach to the peak of a first stent ring and a valley of a second stent ring. The stent ring may be arranged such that the peaks in valleys are in-phase (e.g., the peaks first stent ring share a common centerline with the peaks of the second stent) or out of phase (e.g., the peaks of the first stent ring share a common centerline with the valleys of the second stent ring).

A device in accordance with various embodiments can comprise a first and a second elongated segment, each having two opposing ends and each defining a lumen extending between the ends. The lumens defined by the elongated segments are referred to as primary lumens. Each elongated segment may be comprised of two or more separate subsegments that are joined to form a single elongated segment, as described herein, with the single elongated segment comprised of two or more separate subsegments defining a single lumen and having two opposing ends. Furthermore, any use of the term "elongated segment" in the present disclosure can also include "subsegment." In accordance with various embodiments, the device can comprise two or more elongated segments.

Figure 2:
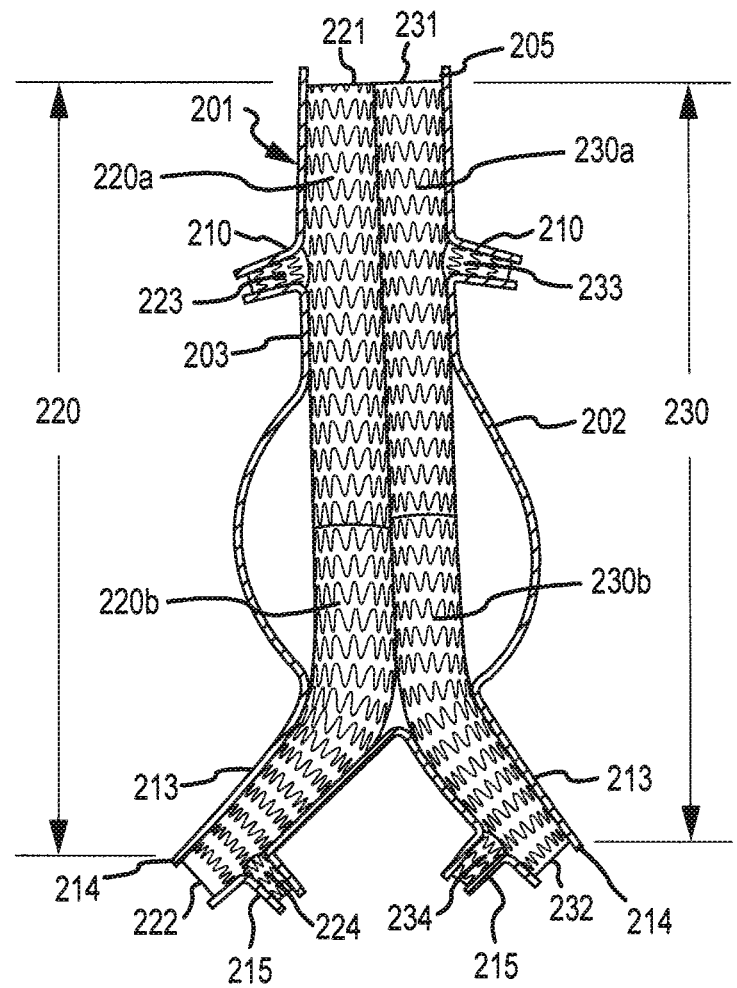
FIG. 2 illustrates a device having a first elongated segment, a second elongated segment, and branch segments in accordance with various embodiments.

In various embodiments and with reference to FIG. 2, a branched stent device comprises two or more elongated segments, such as a first elongated segment 220 and a second elongated segment 230. First elongated segment 220 can be comprised of subsegment 220a and subsegment 220b, and second elongated segment can be comprised of subsegment 230a and subsegment 230b. First elongated segment 220 can have a proximally oriented first end 221 and a distally oriented second end 222, and likewise, second elongated segment 230 can have a proximally oriented first end 231 and a distally oriented second end 232. The elongated segments can be deployed at a treatment site in a vasculature 201 such as an abdominal aorta having an AAA 202 or other body lumen in any suitable configuration. For example, the elongated segments can be installed in a configuration to conduct blood or other bodily fluids between a proximal aortic lumen 205 and distal lumens such as those of the common iliac arteries 213 and/or one or more side branch vessels such as the renal arteries 210 and the internal iliac arteries 215. In the illustrated example, subsegments 220a and 230a of first and second elongated segments 220 and 230 of the device are implanted in the proximal portion of the treatment region to receive blood from proximal aortic lumen 205 and perfuse renal arteries 210 via branch first branch segment 223 and third branch segment 233, and subsegments 220b and 230b of the device conduct blood distally to the external iliac arteries 214 at second ends 222 and 232 of the first and second elongated segments 220 and 230, as well as to internal iliac arteries 215 via second branch segment 224 and fourth branch segment 234. In various other embodiments, the distal ends of elongated segments can be located in other portions of a treatment region, for example, in the common iliac arteries 213 or in a region of normal aorta distal to an aneurism. In accordance with various embodiments, first ends 221 and 231 and second ends 222 and 232 of first elongated segment 220 and second elongated segment 230 may be located in any suitable portion of a treatment region.

In various embodiments, one or more elongated segments may be joined to another medical device. For example, a device comprising two elongated segments, similar to subsegments 220a and 230a, as illustrated in FIG. 2, can be joined at the distal ends of the elongated segments to a proximal end of a bifurcated stent-graft, wherein the bifurcated stent-graft functions to deliver blood to the distal portion of the treatment region. The device comprising two elongated segments can be joined to the bifurcated stent-graft in a substantially fluid-tight manner during deployment of the elongated segments. In this manner, a device in accordance with various embodiments comprising two or more elongated segments and having branch segments, as described below, can be deployed in a proximal portion of a treatment region, such as a proximal aorta having renal artery branches, and joined to a second medical device, for example, a bifurcated stent-graft suitable for installation in a distal portion of a treatment region such as the distal portion of an aneurysm and the common iliac arteries. Any combination of a device in accordance with various embodiments deployed in any portion of a treatment region and joined with any other medical device is within the scope of the present disclosure.

In accordance with various embodiments, a first elongated segment and a second elongated segment have a combined cross section that is substantially conformable to an intraluminal cross section of a body lumen. For example, in any portion of vasculature 201 where first elongated segment 220 and second elongated segment 230 occupy the same cross-sectional profile (e.g., the infrarenal aortic neck 203 or the location of first end 221 of the first elongated segment 220 and first end 231 of the second elongated segment 230 in a proximal aortic lumen 205 as illustrated here), first elongated segment 220 and second elongated segment 230 are substantially conformable to the intraluminal cross section of the vasculature. The substantially conformable cross-sectional profiles of the first elongated segment 220 and the second elongated segment 230 have a combined cross section that substantially approximates the intraluminal cross-sectional profile of vasculature 201. The substantially conformable character of the first elongated segment and the second elongated segment to the intraluminal cross section of the vasculature at a cross section proximal to an aneurysm can contribute to the ability of the device to prevent leakage, thus isolating AAA 202 from fluid pressure and promoting more desirable flow characteristics in the treatment region such as un-obstructed flow, reduced pressure change at the treatment region, evenly distributed flow, steady flow or flow that is otherwise consistent with flow through a healthy body lumen.

In these embodiments, first elongated segment 220 can have any suitable shape. Similarly, second elongated segment 230 can have any suitable shape that is complementary to the shape of first elongated segment 220. This complementary arrangement occurs where the combined cross-sectional profile of first elongated segment 220 and second elongated segment 230, when installed in vasculature 201, substantially approximates the intraluminal cross-sectional profile of vasculature 201 to minimize leakage and improve fluid flow characteristics at the treatment site. For example, first end 221 of first elongated segment 220 can have a substantially elliptical cross-sectional profile when installed at the treatment region corresponding to proximal lumen 205. First end 231 of second elongated segment 230 can have a suitably complementary substantially elliptical cross-sectional profile at the end installed at the treatment region corresponding to proximal lumen 205, where first elongated segment 220 and second elongated segment 230 are installed together. In this embodiment, each of the first end 221 of the first elongated segment 220 and the first end 231 of the second elongated segment 230 is installed on substantially the same level or cross-sectional plane of the vasculature, though in other embodiments they can be installed in other planes or in a longitudinally displaced relationship. Moreover, because of the complementary shape of the each of the ends, the combined profile of the ends form a generally elliptical cross-section that substantially approximates the generally elliptical cross-section of vasculature 201. The substantial conformation of the first elongated segment 220 and the second elongated segment 230 to the intraluminal cross section of proximal lumen 205 allows blood and other bodily fluids to flow through the lumens of the elongated segments approximating vasculature 201.

In various embodiments, the first elongated segment and the second elongated segment can be of any suitable size and shape to provide a combined cross section that is substantially conformable to an intraluminal cross section of a body lumen. The first and second elongated segments can be of sizes and shapes that are complementary to one another and together provide a combined cross section, such as an ellipse, that generally approximates the size and shape of a body lumen and substantially conforms to the intraluminal cross section of a body lumen when deployed together within the lumen.

Figure 3A:
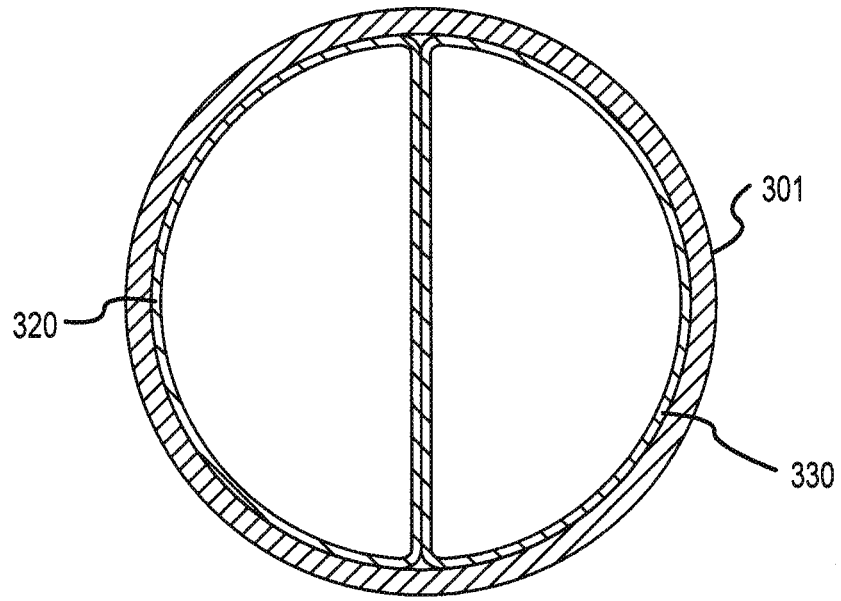
FIGS. 3A-3D illustrate various possible cross-sectional profiles of elongated segments in accordance with various embodiments.
Figure 3B:
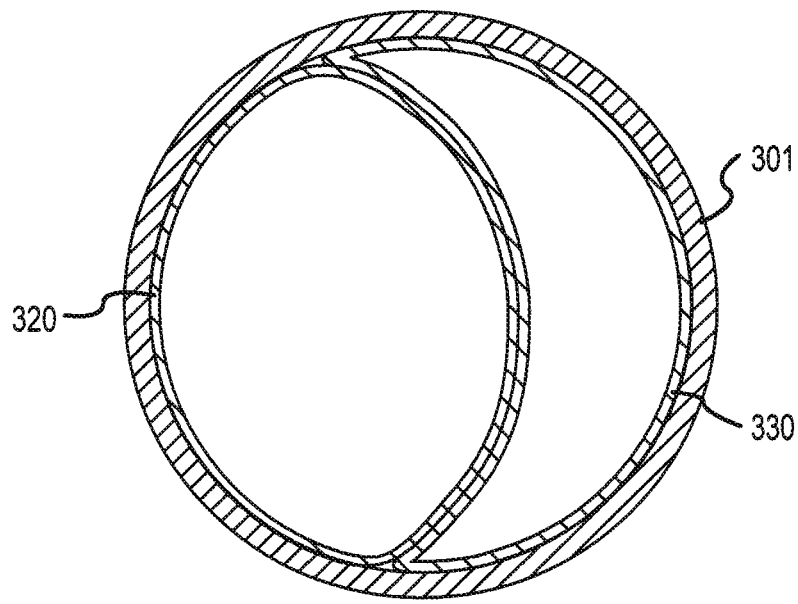

For example, and with reference to FIG. 3A, first elongated segment 320 and second elongated segment 330 can both have generally elliptical cross sections that are complementary to one another such that the combined cross section of the elongated segments substantially conform to the intraluminal cross section of vasculature 301. In various other embodiments and with reference to FIG. 3B, first elongated segment 320 can have a cross-sectional profile that is generally elliptical as illustrated in FIG. 3B, while second elongated segment 330 can a shape that is complementary to the cross section or a portion of the cross section of the first elongated segment 320, such as a crescent shape with an interior arc that complements the elliptical profile of the first elongated segment 320. In accordance with various embodiments, the combined cross-sectional profile of first elongated segment 320 and second elongated segment 330 is generally elliptical and approximates the intraluminal cross section of vasculature 301 regardless of the individual cross-sectional profiles of the component elongated segments.

Figure 3C:
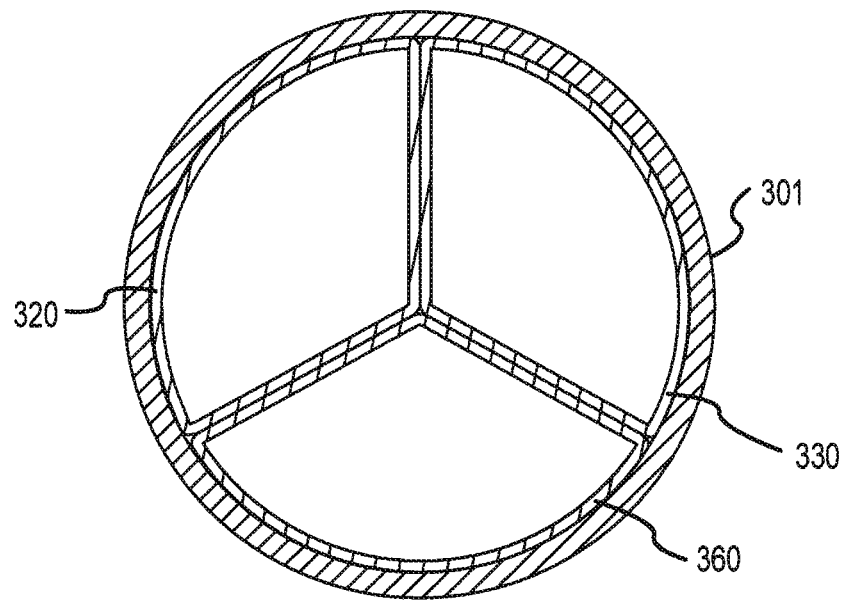
Figure 3D:
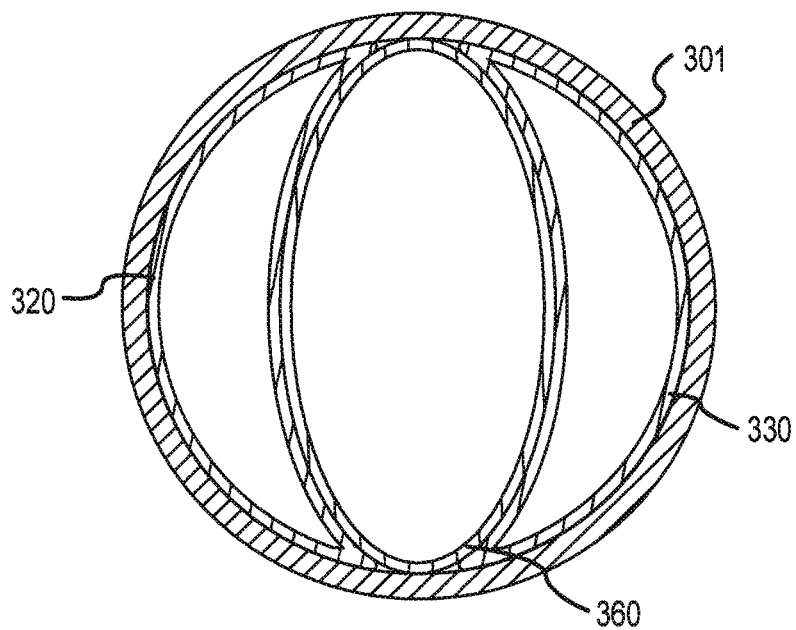

In various embodiments, a device can comprise three or more elongated segments. As for the embodiments described above and as illustrated in FIGS. 3C and 3D, the three or more elongated segments can have shapes that are complementary to one another such that a combined cross section of the elongated segments is substantially conformable to an intraluminal cross section of a body lumen such as an ellipse. For example, each of first elongated segment 320, second elongated segment 330, and third elongated segment 360 can be generally pie-shaped, as illustrated in FIG. 3C. In this configuration, a flat portion of each pie-shaped profile is configured to abut another flat portion of a pie-shaped profile. The curved portion of each pie-shaped profile is configured to approximate a portion of vasculature 301. Other combinations of three or more elongated segments with various complementary cross-sectional profiles, such as a third elongated segment 360 with an elliptical cross section combined with crescent-shaped first elongated segment 320 and second elongated segment 330, as illustrated in FIG. 3D, are also within the scope of the present disclosure. Any number of elongated segments having any combination of cross-sectional profiles that, when installed together, form a combined cross section that is generally elliptical and/or substantially conforms to an intraluminal cross section of a body lumen is within the scope of the present disclosure.

In various embodiments, elongated segments of a device can have cross-sectional profiles that are shaped or formed prior to deployment of the elongated segments, such that the elongated segments take on a predetermined cross-sectional profile upon deployment. For example, elongated segments can be shaped or formed with cross-sectional profiles that are complementary to each other. The elongated segments can be constrained to another cross-sectional profile prior to deployment for insertion and deployment, and upon deployment, the elongated segments can take on their predetermined, complementary cross-sectional profiles that substantially conform to an intraluminal cross section a body lumen.

In various other embodiments, the cross-sectional profile of an individual elongated segment can be determined during deployment, such as by the cross-sectional profile of a balloon expansion device used in deployment. For example, an elongated segment can be plastically deformable, such that it can take on and retain the cross-sectional profile of the balloon expansion devices used to expand and deploy the elongated segment to the implanted state. Balloon expansion devices can be used that are capable of expanding an elongated segment to any suitable size and/or cross-sectional profile, such as circular, elliptical, crescent, pie-shaped or other cross-sectional profiles, such that one or more elongated segments are complementary to one another and substantially conform to the intraluminal cross section of the body lumen in which they are deployed.

In accordance with still other embodiments, the elongated segments can be flexible such that they can accommodate a broad range of cross-sectional profiles and conform in their individual cross-sectional profiles to the intraluminal cross section of the body lumen in which they are deployed. In these embodiments, the intraluminal cross section of the body lumen in which an elongated segment is deployed may be determined by another elongated segment and/or other medical device, either temporary or implanted, during deployment of the flexible elongated segment in the body lumen. Stated differently, the flexible elongated segment may generally lack a predetermined deployed cross-sectional profile, and the cross-sectional profile of the flexible elongated segment is determined by the cross-sectional profile of the body lumen in which it is deployed and any other elongated segments or medical devices that may be deployed therein, regardless of the cross-sectional profile of the body lumen or of those elongated segments or medical devices within the body lumen.

In accordance with various embodiments, one of the elongated segments may have the property of being flexibly able to adapt to the cross-sectional profile of the lumen in which it is located. In various other embodiments, more than one of the elongated segments may be so flexibly adaptable. For example, in a case where two flexibly adaptable elongated segments are deployed together in a body lumen, the two elongated segments would together substantially conform to one another and to the intraluminal cross section of the body lumen in which they are located. In such an embodiment, predetermined complementary cross-sectional profiles for the elongated segments are not required. These embodiments may provide advantages such as the ability to independently position an elongated segment longitudinally and/or rotationally. For example, the absence of predetermined complementarity of one elongated segment with a second elongated segment eliminates the requirement that the two complementary elongated segments be aligned longitudinally and rotationally so as to provide the planned complementary cross-sectional profile.

In accordance with any of the various embodiments described herein, the elongated segments might only be substantially conformable to the intraluminal cross section of a body lumen where there are two or more elongated segments present in the intraluminal cross section of the body lumen. Stated differently, a device in accordance with various embodiments may or may not substantially conform to the intraluminal cross section of a body lumen in cross sections in which only a single elongated segment is located. For example, a device in accordance with various embodiments can comprise two elongated segments of the same length but that are longitudinally displaced from one another within the body lumen, such that only one elongated segment is located at various cross sections within the body lumen. In this example, at the intraluminal cross section(s) of the body lumen that is occupied by a single elongated segment, the elongated segment may not substantially conform to the intraluminal cross section of the body lumen but may only partially occupy the intraluminal cross section.

In accordance with various embodiments, an elongated segment can comprise an open stent region. An elongated segment can comprise an open stent region in any portion of the elongated segment. An open stent region of an elongated segment is a portion of an elongated segment comprising support elements but lacking a covering material or otherwise having a configuration that is perfusable by a fluid. An open stent region of an elongated segment can be located at any part of an elongated segment and can comprise any portion of the elongated segment. For example, an open stent region can be located at an end of an elongated segment or anywhere along the length of the elongated segment. The open stent portion can include the entire circumference of a portion of the length of an elongated segment, or can comprise a portion of the circumference and the length of the elongated segment, forming an open stent window in an area of the elongated segment.

Figure 4:
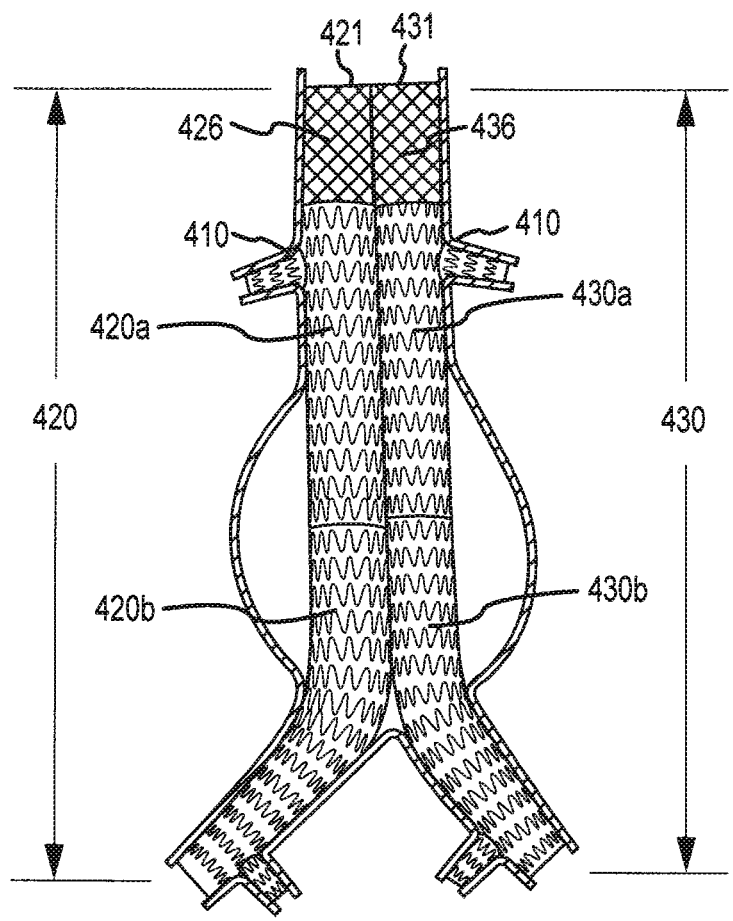
FIG. 4 illustrates a device with a first elongated segment and a second elongated segment having open stent regions at the proximal ends of the elongated segments.

In various embodiments and with reference to FIG. 4, first elongated segment 420 comprising subsegments 420a and 420b and second elongated segment 430 comprising subsegments 420a and 420b can also comprise open stent regions 426 and 436 at first end 421 and first end 431, respectively. As illustrated in FIG. 4, open stent regions 426 and 436 may be located in a region of the elongated segments such that the open region may permit perfusion of branch arteries of the vasculature 401 when deployed. For example, in vasculature, open stent regions 426 and 436 may permit perfusion of the SMA and celiac arteries (not shown) located proximally to renal arteries 410.

In accordance with various embodiments described above, the elongated segments or subsegments of a device may be self-expanding or may be expanded during deployment by a deployment device such as a balloon expansion device. The elongated segments or subsegments thereof may be self-expanding or balloon-expandable to predetermined cross-sectional profiles. The elongated segments or subsegments may also be balloon expandable to cross-sectional profiles conferred by balloon expansion devices having any of a variety of possible cross-sectional profiles. In various embodiments, the elongated segments may be self-expanding or balloon expandable such that they take on the cross-sectional profile of the lumen in which they are located.

In accordance with various embodiments, a device may also comprise branch segments. A branch segment may be engaged to an opening in the side of one of the elongated segments, and the branch segment may further define a branch lumen in fluid communication with one of the primary lumens of the device. A device in accordance with various embodiments may have one branch segment. In various other embodiments, a device may have two or more branch segments. In various embodiments, a single elongated segment may be engaged to two or more branch segments. In other embodiments, one elongated segment may be engaged to one or more branch segments while a second elongated segment is also engaged to one or more branch segments. In accordance with various embodiments and referring again to FIG. 2, the illustrated device comprises four branch segments, with first elongated segment 220 and second elongated segment 230 of the device each having two branch segments. First branch segment 223 is engaged to subsegment 220a of elongated segment 220, and second branch segment 224 is engaged to subsegment 220b of elongated segment 220. Third branch segment 233 is engaged to subsegment 230a of elongated segment 230, and fourth branch segment 234 is engaged to subsegment 230b of elongated segment 230. A device comprising any number of elongated segments, each comprised of any number of subsegments and engaged to any number of branch segments, is within the scope of the present disclosure.

Figures 5A, 5B:
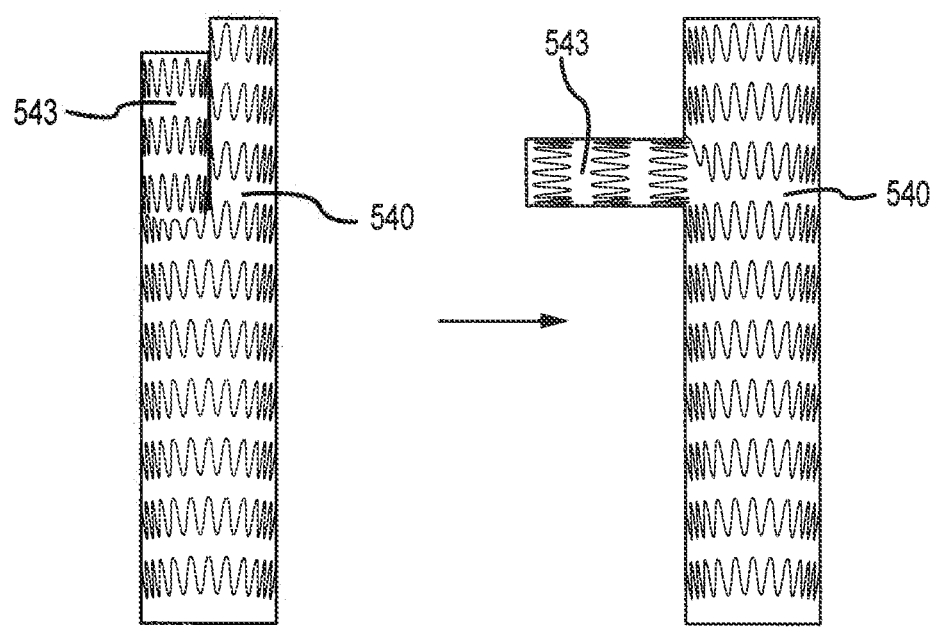
FIGS. 5A and 5B illustrate an elongated segment having a branch segment that is engaged in both an undeployed conformation and a deployed conformation.

In various embodiments, a branch segment may be engaged to an elongated segment as an integral component of the elongated segment. For example, the branch segment may be integrally or permanently engaged to an elongated segment or a subsegment thereof by the support structure and/or the covering material during construction of the elongated segment. FIG. 5B illustrates an elongated segment 540 with a permanently engaged branch segment 543 in accordance with various embodiments. In these embodiments, the support structure of the branch segment may be continuous with the support structure of the elongated segment to which the branch segment is attached, or the support structure of the branch segment may be otherwise permanently engaged to the support structure of the elongated segment, such as by welding, brazing, bonding, wiring, tying, or any other manner of attaching one support structure to another support structure. In various other embodiments, a branch segment may be permanently engaged to an elongated segment or a subsegment thereof by the covering material. For example, the covering material may be formed on a mandrel whose shape defines an elongated segment and an attached branch segment, such that the resultant formed covering material comprises a branch segment defined by covering material that is integrally connected with the covering material defining the elongated segment. In various embodiments, a branch segment may be permanently engaged to an elongated segment by any combination of permanently or integrally connected support structure or covering material.

Figures 6A, 6B:
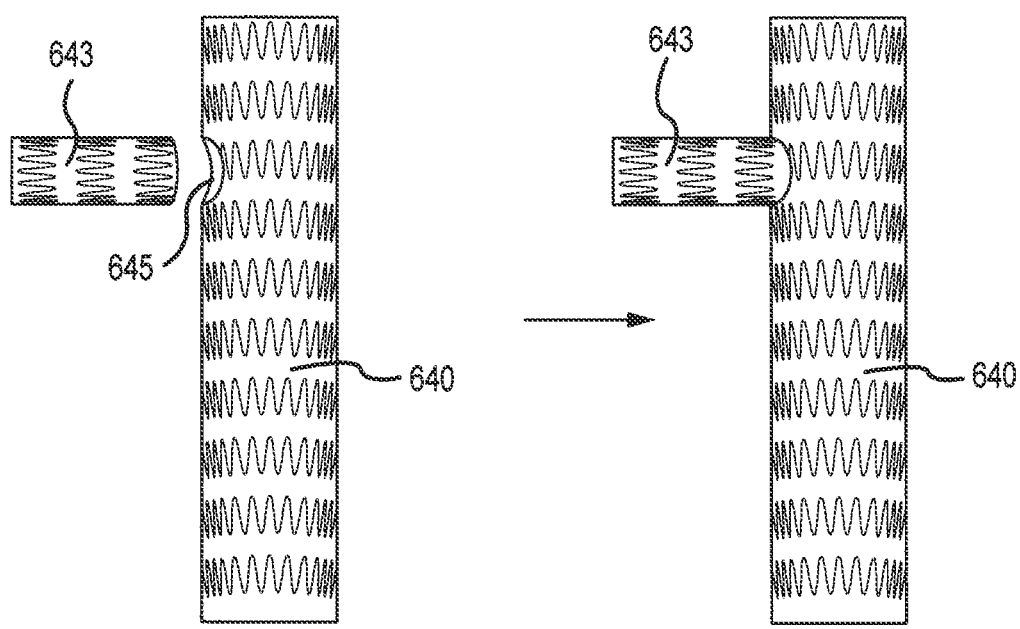
FIGS. 6A and 6B illustrate an elongated segment and a branch segment that is modularly engaged to the elongated segment.

In accordance with other embodiments, a branch segment can be engaged to an elongated segment in a modular fashion after separate construction of an elongated segment and a branch segment. FIGS. 6A and 6B illustrate an elongated segment 640 with a branch segment 643 that is modularly engaged. In such an embodiment, a side branch opening or fenestration 645 can be created in the covering material and/or support element of elongated segment 640, and branch segment 643 can be engaged to elongated segment 640 at the location of fenestration 645 such that the lumen of branch segment 643 is in fluid communication with the lumen of elongated segment 640. In accordance with various embodiments, the branch segment can be engaged to the elongated segment prior to deployment of the device, or the branch segment can be engaged to the elongated segment in situ in the treatment region. The branch segment can be engaged by insertion through the fenestration, for example, by inserting the branch segment into and through the fenestration followed by radial expansion of the branch segment such that an outer surface of the branch segment approximates and seals against the perimeter of the fenestration. In various embodiments, a branch segment can be engaged to an elongated segment by insertion through an internal branch support associated with a fenestration. An internal branch support can comprise, for example, an internal branch channel in the interior of an elongated segment. In such embodiments, a branch segment can be inserted through an internal branch support and an associated fenestration from either the interior of the elongated segment or from the exterior of the elongated segment. Alternatively, the branch segment can be engaged to the perimeter of the fenestration at an end of the branch segment, with the circumference of the end of the branch segment engaged to the perimeter of the fenestration in the elongated segment via connecting means such as by anchoring with hooks, barbs, or any other device or mechanism suitable for attachment of a stent or stent-graft to another stent or stent-graft. In accordance with various embodiments, additional measures can be taken to reinforce the engagement of the branch segment to the elongated region in such an embodiment using any appropriate method and material.

In accordance with various embodiments and regardless of whether a branch segment is permanently or modularly engaged to an elongated segment, the branch segment is engaged to the elongated segment in such a manner that the engagement is substantially fluid-tight. A fluid-tight engagement in accordance with various embodiments can prevent endoleaks and enable a device to provide for the isolation of a treatment region having branch vessels from fluid pressure.

In accordance with various embodiments, a branch segment can be engaged to an elongated segment in a manner that allows the elongated segment and the branch segment to be inserted into a body lumen. In various embodiments and as illustrated in FIG. 5A, branch segment 543 can be positioned against and/or alongside the elongated segment 540 to which it is attached or otherwise constrained along with the elongated segment so that the elongated segment and the branch segment together have a size and conformation that is suitable for insertion into a body lumen, regardless of whether the branch segment is permanently or modularly engaged to the elongated segment.

In accordance with various embodiments, a branch segment is suitable for deployment in a branch vessel. The capacity for the branch segment to be constrained for insertion may be a function of the properties of the branch segment, the manner in which the branch segment is engaged to the elongated segment, the elongated segment, or any combination of these factors. For example, for devices in which the branch segment is permanently engaged to the elongated segment by the covering material, the region in which the branch segment is engaged to the elongated segment may be free of support structures such that the branch segment is free to articulate on a longitudinal axis of the branch segment relative to the longitudinal axis of the elongated segment to which it is engaged. In other embodiments, the support structure of the elongated segment in the area adjacent to where a branch segment is engaged or the support structure by which the branch segment is engaged to the elongated segment can have a configuration that similarly provides for or allows the branch segment to articulate relative to the elongated segment in a manner that facilitates insertion of the device into the body in a constrained form. Any configuration or manner of construction or engagement of the branch segment, the elongated segment, or both, that permits the device to be constrained for insertion into a body lumen is within the scope of the present disclosure.

Likewise, a branch segment can be engaged to an elongated segment in any of a range of possible orientations in accordance with various embodiments. For example, a branch segment may be engaged to an elongated segment such that the longitudinal axis of the branch segment is perpendicular to the longitudinal axis of an elongated segment to which it is engaged. Alternatively, the branch segment can be engaged such that the longitudinal axis of the branch segment is at any angle with respect to the longitudinal axis of an elongated segment. In various embodiments, a branch segment can be curved in the region in which it engages an elongated segment. Any configuration of an intersection by which a branch segment can engage an elongated segment is within the scope of the present disclosure.

In accordance with various embodiments, a branch segment can assist anchoring of an elongated segment. Deployment of a branch segment in a branch vessel can prevent or assist the prevention of migration or slippage of the elongated segment from its implanted position in the body lumen. A branch segment can also facilitate approximation and sealing of a peripheral surface of the elongated segment with an adjacent interior wall of the body lumen.

In accordance with various embodiments, a device can comprise anchors. The anchors can be any structure capable of engaging an adjacent object such as the wall of a vessel or other body lumen or an adjacent medical device or device component. The anchors can be deployed to maintain the implanted position of the device in the body after the device has been deployed. The anchors can further serve to maintain the positions of two or more elongated segments of a device with respect to one another and their positions within the vasculature, such as the respective longitudinal positions of two elongated segments. Anchors may additionally facilitate approximation of the peripheral surfaces of the elongated segments against adjacent surfaces to seal the peripheral surfaces against the adjacent surfaces and prevent fluid leakage into gutters between elongated segments or between an elongated segment and the adjacent vessel wall.

In accordance with various embodiments, an anchor can comprise a branch, as described above, or a hook, barb, or other similar structure. The anchor can be deployed together with deployment of the elongated segment or in a deployment step that is separate from the elongated segment comprising the anchor. For example, in an elongated segment that is deployed by radial expansion using a balloon expansion device, the anchor may deploy simultaneously with radial expansion and deployment of the portion of the elongated segment comprising the anchor.

In accordance with other embodiments, the anchor can be deployed separately from radial expansion of the portion of the device comprising the anchor. In various embodiments, the anchor can be deployed prior to deployment of the elongated segment or following deployment of the elongated segment. Any type of anchor at any location on an elongated segment, deployed in any manner or at any stage of deployment of the device, is within the scope of the present disclosure.

In various embodiments, a device may comprise connectors. In accordance with various embodiments, the connectors facilitate sealing of the device within a body lumen. The connectors can be configured to maintain at least a portion of an outer surface of one of the first elongated segment and the second elongated segment in proximity with an adjacent peripheral surface so as to reduce fluid flow into an area between the outer surface and the adjacent peripheral surface. An outer surface of an elongated segment can be the peripheral or extraluminal surface of the elongated segment at an end of the elongated segment, or it can be a peripheral surface anywhere along the length of the elongated segment. In accordance with various embodiments, sealing along an outer surface of an elongated segment is desirable to prevent fluid leakage between adjacent elongated segments and/or between an elongated segment and the adjacent vessel or body lumen wall and to thus isolate a treated region of a body lumen, such as an aneurysm of the vasculature, from fluid pressure. In accordance with various embodiments, an elongated segment comprises connectors that can be structures such as anchors, articulating flanges, or flaps that function to provide a seal or to contribute to or enhance the capacity of an elongated segment to provide a seal when deployed.

In various embodiments, structures that can function as anchors, as described above, can also serve as connectors, and vice versa, and a single structure or type of structure may serve as both an anchor and a connector.

In various embodiments, the first end of a first elongated segment and the first end of a second elongated segment can be configured with connectors that engage with each other when the elongated segments are implanted in the treatment region. First elongated segment and second elongated segment can each be configured with a suitable connector such as, for example, hooks or barbs. These connectors can be configured to operatively engage one another upon deployment such that the first end of first elongated segment and the first end of second elongated segment are connected together.

In accordance with various other embodiments, an end of a first elongated segment is configured with a connector for associating a portion of the circumference of the elongated segment at an end of the elongated segment with an adjacent peripheral surface. The connector may operatively engage a peripheral surface of a second elongated segment at a position located along the length of the second elongated segment rather than at an end of the second elongated segment. Likewise, the connector may operatively engage an inner surface of the body lumen in which first elongated segment is deployed. In accordance with various embodiments, the connector can serve as an anchor for maintaining the relative position of the device within the body lumen on a longitudinal basis, and/or the connector can serve to approximate a section of the circumference of the device with an adjacent peripheral surface so as to minimize fluid leakage through an area between the device and the adjacent peripheral surface, regardless of whether the adjacent peripheral surface comprises a medical device or the inner surface of the body lumen.

Figure 7A:
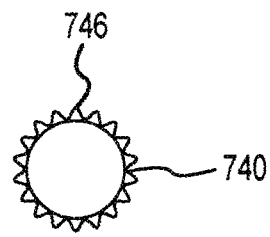
FIGS. 7A and 7B illustrate an elongated segment having flange segments attached at an end of the elongated segment.
Figure 7B:
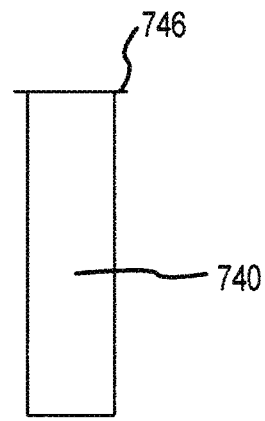

In various embodiments, an elongated segment can comprise a connector consisting of articulating flange segments. FIGS. 7A and 7B illustrate an elongated segment 740 having flange segments 746 in accordance with various embodiments. Articulating flange segments 746 can be attached to elongated segment 740 at an end of the elongated segment or they can be attached on or near the extraluminal surface of the elongated segment. The articulating flange segments 746 can be configured to articulate or otherwise extend outwardly from a longitudinal axis of the elongated segment along at least a portion of the outer surface of the elongated segment, such as a portion of the circumference of the elongated segment at its end.

In various embodiments, the articulating flange segments may comprise support elements and covering material. For example, the articulating flange segments can comprise a series of individual sections of covering material extending from an end of the elongated segments. Each individual section can further include a support element. The covering material and/or support elements of the articulating flange segments can be comprised of covering material and/or support elements that are continuous with and/or an extension of the covering material and/or support element of the elongated segment. In other embodiments, the articulating flange segments can be comprised of covering material and/or support elements that are separate and/or different from those of elongated segment, and the articulating flange segments can be modularly or permanently attached to the elongated segment.

In various embodiments, each articulating flange segment comprises a shape that has a surface area. Each articulating flange segment may be substantially planar. The primary plane defined by a flange segment can be generally perpendicular to radius from a longitudinal axis of the elongated segment. Each flange segment can have any of a variety of shapes, including, for example, square, rectangular, triangular, semicircular, or any other geometric or non-geometric, irregular shape. In various embodiments, at least a portion of one edge of the shape comprised by a flange segment is the edge along which the flange segment is attached to the elongated segment.

In accordance with various embodiments, each individual articulating flange segment can be separate from each other articulating flange segment. Although each flange segment may be separate, a portion of the surface area of each articulating flange segment may overlap with a portion of the surface area of each adjacent articulating flange segment. In accordance with other embodiments, an articulating flange segment can be connected to another articulating flange segment, for example, by covering material and/or by a support element.

In accordance with various embodiments, each flange segment is configured to extend outwardly from a longitudinal axis of an elongated segment. A flange segment can extend outwardly from a longitudinal axis of the elongated segment by articulating, for example, at a joint or other region configured to bend. Such outward articulation can effectively increase the cross-sectional area of the elongated segment and facilitate sealing of the elongated segment against an adjacent peripheral surface such as an adjacent elongated segment or an interior surface of a vessel wall. In various embodiments, the flange segments can be configured to articulate by deforming, such as by bending, pivoting or otherwise changing in shape or conformation with respect to the elongated segment. For example, flange segments attached to the end of an elongated segment may be deformed by a balloon expansion device during or following deployment of the elongated segment, such that the flange segments approximate adjacent peripheral surfaces and the elongated segment substantially conforms to the intraluminal cross section of the body lumen in which it is implanted. The flange segments may articulate at any portion of the flange segment, for example, at a junction of a flange segment with an elongated segment or anywhere along a length of a flange segment. In various embodiments, the flange segments may comprise anchors such as hooks or barbs to assist with maintaining the position of the flange segments adjacent to peripheral surfaces.

Figure 8A:
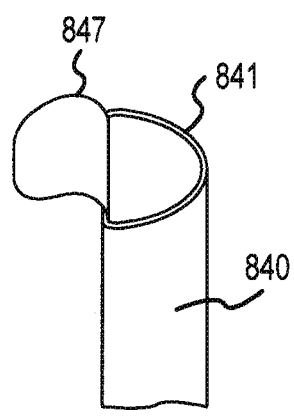
FIGS. 8A-8D illustrate an elongated segment having a flap extending beyond the end of the elongated segment and wrapping around and into the lumen of an adjacent elongated segment.
Figure 8B:
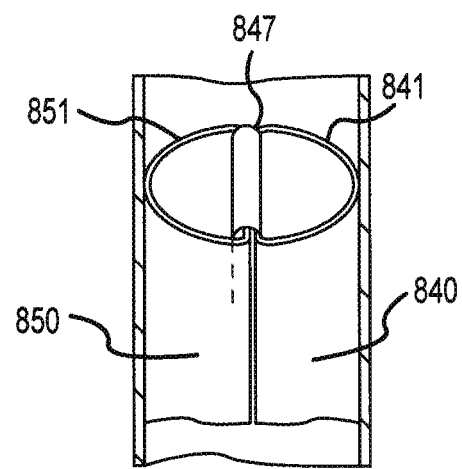
Figure 8C:
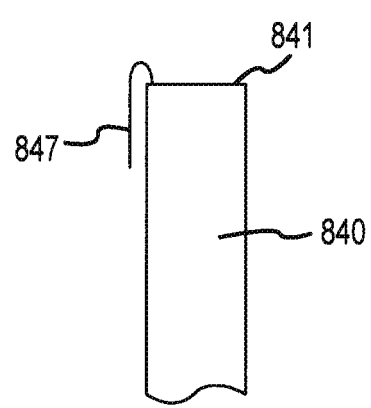
Figure 8D:
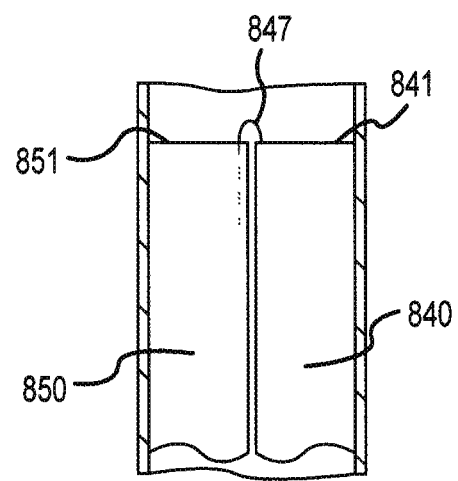

In various embodiments, an elongated segment may comprise a connector that consists of a flap. In accordance with various embodiments and as illustrated in FIG. 8A, elongated segment 840 can have a flap 847 that extends from a portion of end 841 of elongated segment 840. Flap 847 can comprise a section of covering material that extends beyond end 841 of elongated segment 840. Flap 847 comprising covering material may or may not further comprise support elements. In various embodiments, a flap has a thickness that is substantially similar to or the same as the thickness of the covering material of the elongated segment. The covering material comprising a flap can be continuous with the covering material of the elongated segment, or the covering material can be a separate and/or different covering material that may be permanently or modularly engaged to the covering material of the elongated segment. The covering material of a flap can be the same material as the covering material of the elongated segment, or a flap can be comprised of a different material.

In various embodiments, flap 847 may have a width that is a fraction of the circumference of the end of the elongated segment to which it is attached. For example, the flap can have a width that is one third, or one quarter, or one fifth of circumference of the end of the elongated segment. The denominator of the fraction need not be an integer; the width of the flap can be any suitable proportion of the circumference of the end of the elongated segment. The flap also has a length. The length of the flap can be any suitable length that allows the flap of covering material to extend or fold outwardly from a longitudinal axis of the elongated segment and to wrap around and into the lumen of an adjacent elongated segment.

In various embodiments and as illustrated in FIGS. 8A-8D, the width, the length, and the shape of flap 847 is such that the width of the flap can cover a substantial portion of the distance along which a peripheral surface of the end 841 of first elongated segment 840 to which flap 847 is attached and a peripheral surface of end 851 of adjacent elongated segment 850 are adjacent to one another. Likewise, the length of flap 847 is such that the flap can extend into the lumen of adjacent elongated segment 850 and be located adjacent to an intraluminal surface of adjacent elongated segment 850. In this manner, a flap in accordance with various embodiments can occlude or seal an area between elongated segment 840 and adjacent elongated segment 850, thus contributing to preventing leakage between the two elongated segments.

In accordance with various embodiments, a branch segment is configured to be substantially conformable to an intraluminal cross section of a branch vessel lumen in any manner previously described herein with respect to elongated segments. Likewise, a branch segment in accordance with various embodiments can also comprise anchors, connectors, or any of the various other features described herein with respect to elongated segments or devices in general.

The devices, support structures, coatings, and covers, described above, can be biocompatible. As used herein, "biocompatible" means suited for and meeting the purpose and requirements of a medical device, used for either long or short term implants or for non-implantable applications. Long term implants are defined as items implanted for more than 30 days. These support structures, coatings, and secondary structures may be formed of a fluoropolymer such as ePTFE. Alternatively, or in combination with a fluoropolymer, the support structures, coatings, and secondary structures may be formed of biocompatible materials, such as polymers, which may include fillers such as metals, carbon fibers, Dacron, glass fibers or ceramics. Such polymers may include olefin polymers, polyethylene, polypropylene, polyvinyl chloride, polytetrafluoroethylene which is not expanded, fluorinated ethylene propylene 45 copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in support structures, coatings and secondary structures.

These support structures, covers, and coatings may be utilized with bio-active agents. Bio-active agents can be coated onto a portion or the entirety of the support structures, coatings and secondary structures for controlled release of the agents once the support structures, coatings and secondary structures is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with various embodiments, the elongated segments of a device can be positioned within a treatment region independently of one another. Independent positioning of the elongated segments of a device may comprise separate placement of elongated segments of a device in any of a number of combinations with respect to one another, and positioning and/or repositioning of an individual elongated segment may include all manner of possible motions and/or movements, as previously defined herein. Any reference to independent positioning of an elongated segment can also refer to independent positioning of individual subsegments of an elongated segment. Furthermore, individual subsegments of an elongated segment may be positioned independently of one another in any manner described herein with reference to elongated segments. Such independent positioning of components of a device in accordance with various embodiments can be accomplished without sacrificing or negatively affecting other characteristics of the device or its capacity to perform an intended function, for example, the ability of the device to substantially conform to an intraluminal cross section of the body lumen and isolate a treatment region from fluid pressure.

Figure 9A:
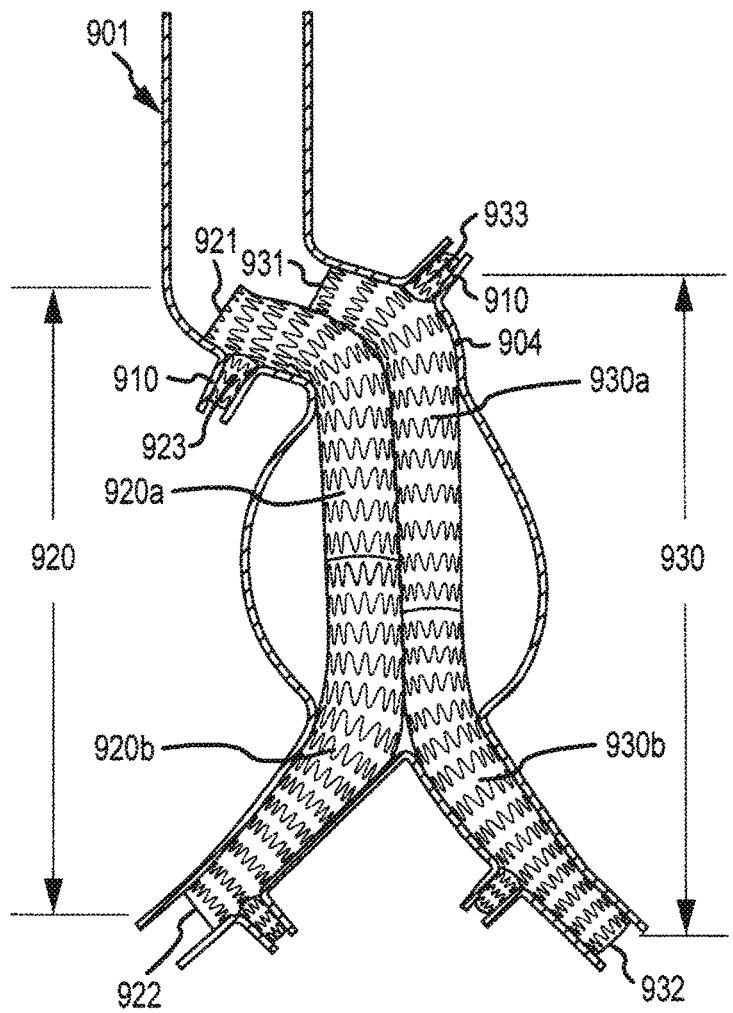
FIGS. 9A-9C illustrate a profile view and cross-sectional views of a device comprising two longitudinally displaced elongated segments in a vasculature having an angulated infrarenal aortic neck.

For example and as illustrated in FIG. 9A, for a device comprising two elongated segments, first elongated segment 920 comprising subsegments 920a and 920b can be positioned and implanted in a longitudinally displaced configuration in the treated vasculature 901 with respect to second elongated segment 930 comprising subsegments 930a and 930b (i.e., the first end 921 and first end 931 and/or the second end 922 and second end 932 of the first and second elongated segments may not be located at the same longitudinal position within a treated vessel). In such an example and as will be described in additional detail herein, both first elongated segment 920 and second elongated segment 930 can be inserted into and co-occupy various transverse sections of the vasculature 901, and one of the elongated segments can be deployed to an expanded state, while both elongated segments retaining the capacity to be independently positionable, as described herein, without the need for recapture of the deployed elongated segment prior to independent positioning of either device component.

In accordance with various embodiments, the capacity of the elongated segments of the device or system to be independently positionable longitudinally may facilitate the ability of the device to conform to irregular vasculature such as the abdominal aorta illustrated in FIG. 9A depicting angulation of the infrarenal aortic neck. For example, first elongated segment 920 may be located on the inside curve or angle of an angulated infrarenal aortic neck 904 and have one longitudinal position within the aorta to facilitate proximal attachment of the elongated segment and placement of branch segment 923 in one renal artery 910. Second elongated segment 930 may be located on the outside curve or angle of the angulated infrarenal aortic neck 904 and have a different longitudinal position within the aorta relative to first elongated segment 920, with the differential longitudinal position being necessary or convenient for optimal proximal attachment of the second elongated segment and placement of branch segment 933 in the other renal artery 910.

Figure 9B:
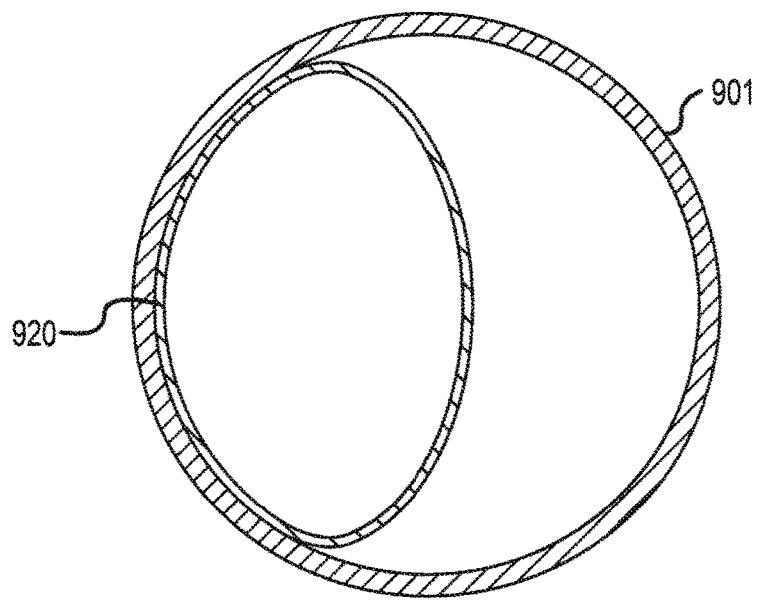
Figure 9C:
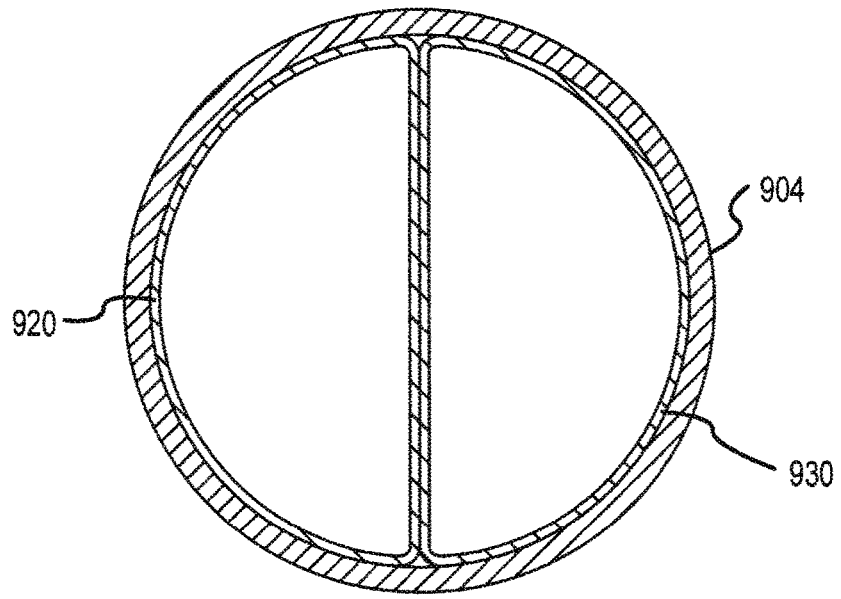

In accordance with various embodiments and as illustrated in FIGS. 9A-9C, the first and second elongated segments in an longitudinally displaced arrangement may still co-occupy at least one cross section of the aorta proximal to the aneurysm and substantially conform to the intraluminal cross section of the aorta at that cross section, effectively isolating the aneurysm from fluid pressure at the proximal end in a manner that is adaptable to an angulated infrarenal aortic neck 904. For example and with reference to FIGS. 9A and 9B, first end 921 of first elongated segment 920 may be longitudinally displaced from first end 931 of second elongated segment 930 such that first end 921 of first elongated segment 920 partially occupies an intraluminal cross section of vasculature 901. With reference to FIGS. 9A and 9C, at a more distal cross section of vasculature 901 through angulated infrarenal aortic neck 904, both first elongated segment 920 and second elongated segment 930 occupy and substantially conform to the intraluminal cross section of the vasculature.

In other examples in accordance with various embodiments of the present disclosure, a longitudinally displaced arrangement of elongated segments can be used to accommodate severe angulation of the aorta proximal to the aneurysm or treatment regions wherein branch arteries such as the renal arteries are located immediately adjacent to or within the region of the aortic aneurysm, such as in a juxtarenal or a suprarenal aortic aneurysm. In accordance with various embodiments, a first elongated segment and a second elongated segment may substantially conform to an intraluminal cross section of an abdominal aorta at a cross section that is proximal to the renal arteries (i.e., suprarenal). In various embodiments, the elongated segments used in such applications may comprise branch segments. Branch segments in accordance with various embodiments can be deployed in a branch vessel such as a renal artery and attach to a side opening of an elongated segment such that a branch lumen of the branch segment is in fluid communication with the lumen of the elongated segment. In such embodiments, the branch segment is engaged to the elongated segment in a manner that maintains fluid communication between a proximal region of the aorta and the branch vessel while preventing fluid leakage at the site of engagement, notwithstanding the pararenal location of the aneurysm.

In accordance with various embodiments, elongated segments or portions thereof may be independently positionable with respect to another elongated segment. In various embodiments, in addition to independent longitudinal positioning, an elongated segment may be moved laterally (i.e., to a different radial position within a body lumen), rotationally, torsionally, or angularly, or may be moved and positioned using any combination of the aforementioned categories of movement. For example, an elongated segment may be rotated about a predominantly longitudinal axis independently of another elongated segment to orient a branch segment with a branch vessel or to orient a portion of the cross-sectional profile of the elongated segment with a complementary elongated segment. Likewise, an elongated segment may be moved to various radial positions within a body lumen, for example, from a more anterior position within a body lumen to a more lateral position within a body lumen.

Similarly, the angle of an elongated segment or a portion of an elongated segment may be changed within a body lumen independently of another elongated segment. For example, the angle of an elongated segment or a section thereof, such as an end, may be changed such that a longitudinal axis of an elongated segment or a portion thereof is skewed with respect to a longitudinal axis of a body lumen or a portion thereof. A capacity of the separate elongated segments of a device for independent positioning using any type of movement in any possible direction is within the scope of the present disclosure. Independent movement and positioning of elongated segments of a device such as that described herein facilitates adaptation of the components of a device to any given anatomical configuration of a treatment site so that the combined cross section of the elongated segments of a device may substantially conform to an intraluminal cross section of a body lumen. Independent movement and positioning may further facilitate placement of branch segments within branch vessels and optimal flow of fluid through a vessel and associated branch vessels without endoleaks in a manner that approximates a normally functioning, intact vasculature.

In various embodiments, a device may be deployed using any suitable device delivery system. The device delivery system may comprise one or more catheters, guidewires, or other suitable conduit for delivering an elongated segment to a treatment region. In these embodiments, the catheters, guidewires, or conduits may comprise lumens configured to receive inputs and/or materials from the proximal end of the medical device delivery system and conduct the inputs and/or materials to the elongated segment at the treatment region.

In various embodiments, various components of the devices disclosed herein are steerable. For example, during deployment at a treatment site, one or more of the elongated segments may be configured with a removable steering system that allows an end of the elongated segment to be biased or directed by a user. A removable steering system in accordance with various embodiments can facilitate independent positioning of an elongated segment and may provide for the ability of a user to accomplish any of the types of movements previously described, such as longitudinal movement, lateral movement, rotational movement, or angular movement.

In accordance with various embodiments, a method of installing an implantable medical device into the body of a patient comprises deploying two or more elongated segments in a target region of the vasculature. In various embodiments, a method of installing an implantable medical device further comprises deploying a branch segment in a branch vessel.

In various embodiments, a method of installing an implantable medical device in the body of a patient comprises deploying a first elongated segment from a first elongated segment constrained state to a first elongated segment implanted state in a target region of the vasculature and deploying a second elongated segment from a second elongated segment constrained state to a second elongated segment implanted state in the target region of the vasculature. In accordance with various embodiments, the first elongated segments and the second elongated segments are substantially parallel to one another in at least a portion of the target region of the vasculature. Substantially parallel in accordance with various embodiments means generally aligned with each other within a vasculature or within a portion of the vasculature. Elongated segments that may have divergent longitudinal axes at any given cross section are nonetheless within the scope of the present disclosure. In accordance with various embodiments, deploying an elongated segment may comprise deploying and joining two or more subsegments. Subsegments can be separately inserted and deployed, with the subsegments being joined together during subsegment deployment, and the entire process comprising deployment of an elongated segment.

In various embodiments, a method of installing an implantable medical device into the body of a patient comprises deploying a branch segment into a branch vessel. A branch segment lumen of the branch segment in accordance with various embodiments is in fluid communication with a primary lumen of one of the first and second elongated segments. In various embodiments, deploying a branch segment may comprise deploying a constrained branch segment from a constrained state to an implanted state within a branch vessel.

In accordance with various embodiments, deploying a branch segment may comprise attaching a branch segment to one of the first elongated segment and the second elongated segment. A branch segment may be attached to an elongated segment by inserting a branch segment into a side opening of one of the elongated segments or by engaging the end of a branch segment to the side opening of the elongated segment. Deploying a branch segment may further comprise inserting a branch segment into an internal branch support of the elongated segment. Insertion of a branch segment into an internal branch support may be done from within the lumen of the elongated segment or from the outside of the elongated segment to which the branch segment is engaged. Furthermore, deployment of a branch segment in accordance with various embodiments may comprise creation of a side opening in and/or engagement of a branch segment with an elongated segment, regardless of whether the elongated segment is in the constrained or implanted state, following insertion of the elongated segment into the target region of the vasculature.

In various embodiments, installing an implantable medical device into the body of a patient may comprise deploying at least two branch segments. In accordance with various embodiments, installing a medical device can comprise deploying a first elongated segment having at least two branch segments or deploying a first elongated segment and a second elongated segment, each elongated segment having at least one branch segment.

In various embodiments, deploying a branch segment into a branch lumen comprises deploying one or more branch segments into one or more branch vessels. Branch vessels in accordance with various embodiments can include, for example, renal arteries, internal iliac arteries, the celiac artery, or the SMA. Any other branch vessel of a vasculature or any other body lumen is within the scope of the present disclosure.

In accordance with various embodiments, installing an implantable medical device can comprise repositioning an elongated segment. In various embodiments, an elongated segment can be repositioned after deployment of the elongated segment to the target region without the need to reconstrain the elongated segment after deployment. For example, during deployment of a medical device comprising two or more elongated segments, one of the elongated segments can be inserted into the target region of the vasculature and deployed from a constrained state to an elongated state such as a radially expanded state. In such an example, the deployed elongated segment can be repositioned, such as by moving the proximal end of the elongated segment to a lower level (i.e., a more distal position within the vasculature), without reconstraining the elongated segment. Repositioning without reconstraining may be performed regardless of whether another elongated segment has been inserted into the target region. For example, an elongated segment may be deployed to an implanted state in a target region of the vasculature and repositioned before another elongated segment has been inserted, or deployment and repositioning may be performed after insertion but prior to deployment of another elongated segment.

In various embodiments, installing an implantable medical device may comprise positioning an open stent region of an elongated segment adjacent to an opening of a branch vessel. In accordance with various embodiments, a portion of an elongated segment, for example, a proximal or first end, can comprise an open stent region with a support element lacking a covering material. A method of installing an implantable medical device comprising an open stent region can include positioning the elongated segment such that the open stent region is adjacent to and allows perfusion of an opening of a branch vessel, such as a celiac artery or a SMA. An elongated segment can comprise an open stent region at any portion of the elongated segment, and positioning of the open stent region of an elongated segment can comprise positioning the open stent adjacent to the opening of any branch vessel of a vasculature.

In various embodiments, installing an implantable medical device can comprise deploying a connector. In accordance with various embodiments, one of the first elongated segment and the second elongated segment comprises a connector for maintaining the position of the elongated segment with respect to the vasculature and the other elongated segment. A connector can comprise a hook, barb, or any other structure for operationally engaging a portion of an elongated segment with an adjacent structure, such as an interior surface of the vasculature or an exterior surface or connector of another elongated segment. In various embodiments, a method of installing a medical device can comprise deploying a connector simultaneously with deployment of the elongated segment to an implanted state. In other embodiments, deployment of a connector may occur separately from deployment of the elongated segment, including deployment of the connector either before or after deployment of the elongated segment to an implanted state.

In accordance with various embodiments, any logical order of any of the above described aspects of a method of installing an implantable medical device is within the scope of the present disclosure. For example, two or more elongated segments may be inserted and/or deployed in a target region of a vasculature prior to deploying a branch segment in a branch vessel. Alternately, a first elongated segment and at least one branch segment may be deployed prior to insertion and/or deployment of a second elongated segment. Any possible permutation of insertion and/or deployment of two or more elongated segments in a target region of a vasculature, including any possible permutation of deploying at least one branch segment in a branch vessel of the target region, is within the scope of the present disclosure. Likewise, any possible permutation of additional steps such as repositioning an elongated segment, positioning an open stent region, and/or deploying a connector along with the steps of deploying elongated segments and/or branch segments is also within the scope of the present disclosure. Any presented order of method steps is intended for illustrative purposes only and not by way of limitation.

The devices and methods described herein may provide benefits such as modularity that enable various individual device components to be selected and installed together at a treatment site and increase the ability of a physician to adaptably treat an increased range of anatomical variation. Devices in accordance with the present disclosure permit sizing and configuration of elongated segment and/or branch segment components that can conform to the specific geometry of the vasculature at a treatment site.

The devices and methods disclosed herein can provide the physician with a broader range of treatment options as compared to selecting from a limited range of predetermined options. For example, a device in accordance with various embodiments can comprise two elongated segments selected by the physician to provide a combined cross section suitable to approximate the cross section of a vasculature at a treatment site of a patient, and the device may further comprise branch segments that may be added to the elongated segments in a fashion that is more customizable and adapted to the specific needs and anatomy of the patient, with the location at which the branch segment is connected to the elongated segment and the branch segment size determined by the physician based on the anatomy of the patient and with the branch segment added to the device in a modular manner.

The modular nature of devices and systems in accordance with the present disclosure may confer the benefits as described above while reducing the number of separate devices that must be manufactured by a producer or purchased and stocked by a treating facility. The devices and systems of the present disclosed herein may provide the further benefit of reducing the undeployed sizes or diameters of medical devices and the trauma associated with insertion and deployment relative to a treatment device comprising a single component inserted into the region to be treated.

For the avoidance of doubt, the device and methods disclosed herein have been described in the context of providing therapy to the vasculature, however, it should be understood that these devices may be implantable in any suitable body lumen.

Thus, the branched adaptable stent devices and method described herein provides a mechanism to substantially approximate various anatomical configurations of the vasculature or other body lumens, including branch vessel lumens, at a treatment region to minimize leakage around the medical device(s) at the treatment region and isolate a treatment region from fluid pressure.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of installing an implantable medical device into a body of a patient comprising:
    deploying a first elongated segment from a first elongated segment constrained state to a first elongated segment implanted state in a target region of a vasculature, the first elongated segment having a proximal end and a distal end;
    deploying a second elongated segment after deploying the first elongated segment, the second elongated segment being deployed from a second elongated segment constrained state to a second elongated segment implanted state in the target region of the vasculature, the second elongated segment having a proximal end and a distal end, wherein the second elongated segment is deployed adjacent and substantially parallel to the first elongated segment between the first elongated segment and the vasculature such that the first and second elongated segments extend along at least a portion of the target region of the vasculature and the proximal end of the second elongated segment is longitudinally displaced from the proximal end of the first elongated segment;
    extending a connector between the first elongated segment to the proximal end of the second elongated segment to secure the proximal end of the second elongated segment relative to the first elongated segment, the connector including at least one of a flange and a flap; and
    deploying a branch segment in a branch vessel;
    wherein a combined cross section of the first elongated segment and the second elongated segment substantially fills an intraluminal cross section of the vasculature in the implanted states, and
    wherein the branch segment extends through a fenestration in one of the first elongated segment and second elongated segment so that a branch segment lumen of the branch segment extends to a primary lumen of the one of the first elongated segment and the second elongated segments.

2. The method of claim 1, wherein deploying the first elongated segment comprises joining two or more subsegments and deploying the second elongated segment comprises joining two or more segments.

3. The method of claim 1, wherein deploying the branch segment further comprises attaching the branch segment to one of the first elongated segment and the second elongated segment.

4. The method of claim 3, wherein attaching the branch segment to one of the first elongated segment and the second elongated segment comprises inserting the branch segment into an internal branch support the one of the first elongated segment and the second elongated segment.

5. The method of claim 1, further comprising deploying at least two branch segments.

6. The method of claim 1, wherein at least one of the first elongated segment and the second elongated segment are repositioned after deployment to the target region without reconstraining one of the first elongated segment and the second elongated segment after deployment.

7. The method of claim 1, further comprising positioning an open stent region of one of the first elongated segment and the second elongated segment adjacent to an opening of the branch vessel to allow fluid communication between the branch vessel and the primary lumen of one of the first elongated segment and the second elongated segment.

8. The method of claim 1, wherein at least one of the first elongated segment and the second elongated segment comprises a connector.

9. The method of claim 8, further comprising deploying the connector.

10. The method of claim 1, wherein the branch vessel is a member of the group consisting of a renal artery, an internal iliac artery, a celiac artery, and a superior mesenteric artery.

11. The method of claim 1, further comprising joining an implanted medical device comprising the first elongated segment, the second elongated segment, and the branch segment to a second medical device.

12. A method of installing an implantable medical device into a body of a patient comprising:
    deploying a first elongated segment from a first elongated segment constrained state to a first elongated segment implanted state in a target region of a vasculature;
    deploying a second elongated segment that is separate from the first elongated segment, the second elongated segment being deployed from a second elongated segment constrained state to a second elongated segment implanted state in the target region of the vasculature, wherein a combined cross section of the first elongated segment and the second elongated segment substantially fills an intraluminal cross section of the vasculature in the implanted states;
    extending a connector between the first elongated segment and the second elongated segment to secure the first elongated segment to the second elongated segment; and deploying a branch segment in a branch vessel after deployment of the first and second elongated segments, wherein the branch segment extends through a fenestration in one of the first elongated segment and second elongated segment so that a branch segment lumen of the branch segment extends to a primary lumen of the one of the first elongated segment and the second elongated segments.

13. The method of claim 12, wherein deploying the first elongated segment further comprises joining two or more subsegments and deploying the second elongated segment further comprises joining two or more subsegments.

14. The method of claim 12, wherein deploying the branch segment further comprises attaching the branch segment to one of the first elongated segment and the second elongated segment.

15. The method of claim 14, wherein attaching the branch segment to one of the first elongated segment and the second elongated segment comprises inserting the branch segment into an internal branch support the one of the first elongated segment and the second elongated segment.

16. The method of claim 12, further comprising deploying at least two branch segments.

17. The method of claim 12, wherein at least one of the first elongated segment and the second elongated segment are repositioned after deployment to the target region without reconstraining one of the first elongated segment and the second elongated segment after deployment.

18. The method of claim 12, further comprising positioning an open stent region of one of the first elongated segment and the second elongated segment adjacent to an opening of the branch vessel to allow fluid communication between the branch vessel and the primary lumen of one of the first elongated segment and the second elongated segment.

19. The method of claim 12, wherein the connector comprises a flap, wherein a peripheral surface of the first elongated segment and a peripheral surface of the second elongated segment engage one another along an interface having a width, and wherein the flap has a width corresponding to the width of the interface between the first and second elongated segments.

20. The method of claim 12, wherein the flap has a width that is between one third and one fifth of the circumference of the proximal end of the first elongated segment.

21. The method of claim 12, wherein the connector is a flap having length, and further wherein extending the connector between the first elongated segment and the second elongated segment to secure the first elongated segment to the second elongated segment includes extending a portion of the length of the flap into the second elongated segment.

22. A method of installing an implantable medical device into a body of a patient comprising:
   deploying a first elongated segment from a first elongated segment constrained state to a first elongated segment implanted state in a target region of a vasculature;
   deploying a second elongated segment that is separate from the first elongated segment, the second elongated segment being deployed from a second elongated segment constrained state to a second elongated segment implanted state in the target region of the vasculature, wherein a combined cross section of the first elongated segment and the second elongated segment substantially fills an intraluminal cross section of the vasculature in the implanted states;
   extending a connector comprising at least one of a flange and a flap between the first elongated segment and the second elongated segment to secure the first elongated segment to the second elongated segment.

23. The method of claim 22, wherein the connector is a flap having length, and further wherein extending the connector between the first elongated segment and the second elongated segment to secure the first elongated segment to the second elongated segment includes extending the flap from a proximal end of the first elongated segment over the proximal end of the second elongated segment and into the second elongated segment.

* * * * *